US00PP32150P2

(12) United States Plant Patent
Christensen

(10) Patent No.: US PP32,150 P2
(45) Date of Patent: Sep. 1, 2020

(54) ***PEPEROMIA* PLANT NAMED 'QUITO'**

(50) Latin Name: *Peperomia caperata*
Varietal Denomination: Quito

(71) Applicant: Per Christensen, Odense S (DK)

(72) Inventor: Per Christensen, Odense S (DK)

(73) Assignee: Gartneriet Tingdal Aps, Odense S (DK)

( * ) Notice: Subject to any disclaimer, the term of this patent is extended or adjusted under 35 U.S.C. 154(b) by 0 days.

(21) Appl. No.: 16/602,708

(22) Filed: Nov. 22, 2019

(51) Int. Cl.
*A01H 5/00* (2018.01)

(52) U.S. Cl.
USPC ..... Plt./373

(58) Field of Classification Search
USPC ..... Plt./373
CPC ..... A01H 5/00
See application file for complete search history.

*Primary Examiner* — Annette H Para

(57) ABSTRACT

A new cultivar of *Peperomia* plant named 'Quito' that is characterized by leaves that are orange-brown on both the upper and lower surfaces, a large number of leaves and a compact habit.

1 Drawing Sheet

Botanical classification: *Peperomia caperata.*
Variety denomination: 'Quito'.

BACKGROUND OF THE INVENTION

The present invention relates to a new and distinct cultivar of *Peperomia* plant botanically known as *Peperomia caperata* and hereinafter referred to by the cultivar name 'Quito'.

'Quito' was discovered as a naturally occurring leaf mutation of *Peperomia caperata* 'Red Luna' (not patented) in May of 2015. The new cultivar was discovered in a population of *Peperomia* 'Red Luna' plants in a controlled environment and cultivated area of Odense, Denmark.

Asexual reproduction of the new cultivar 'Quito' first occurred by leaf cuttings in May of 2016 in Odense, Denmark. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Quito'. These traits in combination distinguish 'Quito' as a new and distinct cultivar apart from other existing varieties of *Peperomia* known by the inventor.

1. *Peperomia* 'Quito' exhibits orange-brown leaves on both upper and lower surfaces.
2. *Peperomia* 'Quito' exhibits a large number of leaves.
3. *Peperomia* 'Quito' exhibits a compact habit.

The closest comparison cultivars are *Peperomia* 'Schumi Red' (not patented) and *Peperomia* 'Lilian' (not patented). 'Quito' is distinguishable from 'Schumi Red' by the following characteristics:

1. *Peperomia* 'Quito' exhibits orange-brown leaves on both upper and lower surfaces. In comparison, the leaves of 'Schumi Red' are red on both the upper and lower surfaces.

2. *Peperomia* 'Quito' exhibits a less compact plant habit than the plant habit of 'Schumi Red'.

'Quito' is distinguishable from 'Lilian' by the following characteristics:

1. *Peperomia* 'Quito' exhibits orange-brown leaves on both upper and lower surfaces. In comparison, the leaves of 'Lilian' are green on both the upper and lower surfaces.

'Quito' is distinguishable from the parent plant *Peperomia* 'Red Luna', by the following characteristics:

1. The leaves of 'Quito' are orange-brown on both the upper and lower surfaces. In comparison, the leaves of the parent plant are purple-red on both the upper and lower surfaces.

BRIEF DESCRIPTION OF THE DRAWING

The accompanying photograph illustrates the distinguishing traits of *Peperomia* 'Quito'. The photograph shows an overall view of a 30 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Quito'. Data was collected in Odense, Denmark from 30 week old plants grown in a glass greenhouse in 14.0 cm. diameter containers. The time of year was Autumn and the temperature range was 20-23 degrees Centigrade during the day and 18-20 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Quito' has not been tested under all possible conditions and phenotypic differences may be observed with variations in environmental, climatic, and cultural conditions, however, without any variance in genotype.

Botanical classification: *Peperomia caperata* 'Quito'.

Annual or perennial: Perennial.

Parentage: 'Quito' is a naturally occurring leaf mutation of *Peperomia* 'Red Luna'.

Plant type: Potted plant.

Growth habit: Rosette of leaves forming very short thick stems.

Plant shape: Flattened globe shaped.

Suitable container size: 7 cm. pots or larger.

Plant height to top of foliage: Average 18.3 cm.

Plant width: Average 28.8 cm.

Vigor: Moderate to high.

Growth rate: Moderate.

Low temperature tolerance: 10° Centigrade.

High temperature tolerance: 35° Centigrade.

Propagation: Leaf cuttings.

Time to initiate roots (summer): 28 days at 20° C.

Time to initiate roots (winter): 35 days at 20° C.

Time to produce a rooted cutting (summer): 80 days at 20° C.

Time to produce a rooted cutting (winter): 100 days at 20° C.

Crop time: Approximately 30 weeks in Odense, Denmark.

Root system: Fine and fibrous.

Plant fragrance: None.

Stem:

*Branching habit*.—Very short thick main stems branching into lateral rosettes of leaves.

*Pinching*.—Not required.

*Number of main stems per plant*.—Average 3.

*Number of lateral branches per plant*.—Average 15.

*Lateral branch dimensions*.—Average 1.9 cm. in length and 0.8 cm. in width.

*Internode length*.—Less than 0.1 cm.

*Stem appearance*.—Succulent.

*Stem shape*.—Rounded.

*Stem texture*.—Smooth.

*Stem luster*.—Glossy.

*Stem pubescence*.—Absent.

*Stem angle*.—Average 20 degrees.

*Stem strength*.—Moderately strong.

*Stem color* (*young*).—187B.

*Stem color* (*mature*).—N186C.

*Internode color*.—N186C.

Foliage:

*Leaf arrangement*.—Alternate.

*Compound or single*.—Single.

*Quantity of leaves per lateral branch*.—Average 13.

*Leaf shape*.—Cordate.

*Leaf aspect*.—Slightly concave.

*Leaf apex*.—Broad bluntly acute.

*Leaf base*.—Hastate, lobes slightly overlapping.

*Leaf dimensions*.—Average 6.3 cm. in length and 5.4 cm. in width.

*Texture upper surface*.—Glabrous, slightly leathery, strongly bullate, moderately covered with small glands, 0.2 mm. in diameter and 187D in color.

*Texture lower surface*.—Glabrous, moderately leathery.

*Leaf luster upper surface*.—Slightly glossy.

*Leaf luster lower surface*.—Matte, velvety.

*Pubescence*.—Absent (both surfaces).

*Leaf margin*.—Entire, slightly revolute.

*Leaf lobed*.—Not lobed.

*Leaf rugose*.—Not rugose (both surfaces).

*Venation pattern*.—Parallel, strongly furrowed.

*Young leaf color* (*upper surface*).—187A to 187B.

*Young leaf color* (*lower surface*).—183D.

*Mature leaf color* (*upper surface*).—178B, tinged 152B to 152C.

*Mature leaf color* (*lower surface*).—183D to 185C.

*Vein color* (*upper surface*).—178A, tinged 152B.

*Vein color* (*lower surface*).—183B.

Petiole:

*Petiole dimensions*.—Average 11.4 cm. in length and 0.4 cm. in diameter.

*Petiole texture*.—Glabrous.

*Petiole luster*.—Moderately glossy on both sides.

*Petiole pubescence*.—Absent.

*Petiole strength*.—Low.

*Petiole color* (*both sides*).—184A.

Flower: 'Quito' has not produced flowers to date.

Fruit and seed: 'Quito' has not produced fruit or seed to date.

Disease and pest resistance: Disease and pest resistance do not differ from other *Peperomia* varieties.

The invention claimed is:

1. A new and distinct variety of *Peperomia* plant named 'Quito' as described and illustrated.

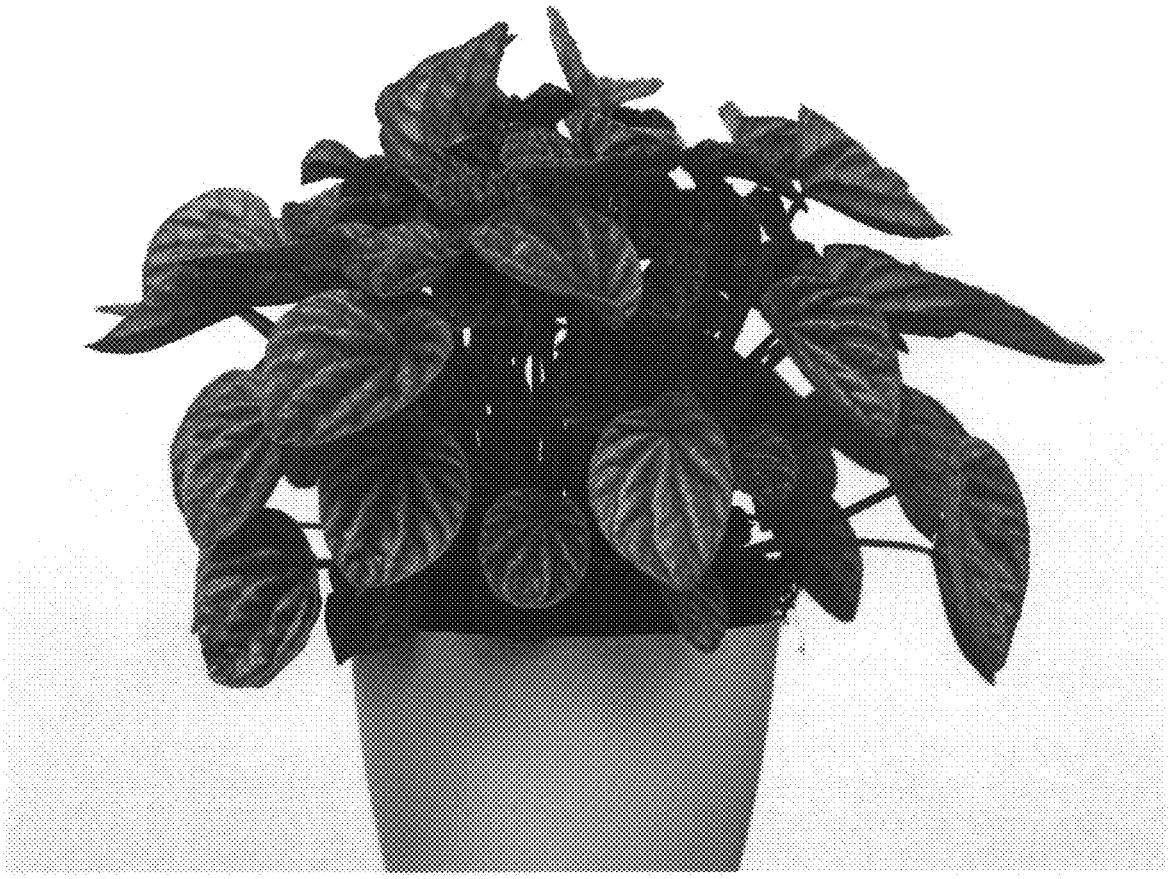

* * * * *